Figure 1:
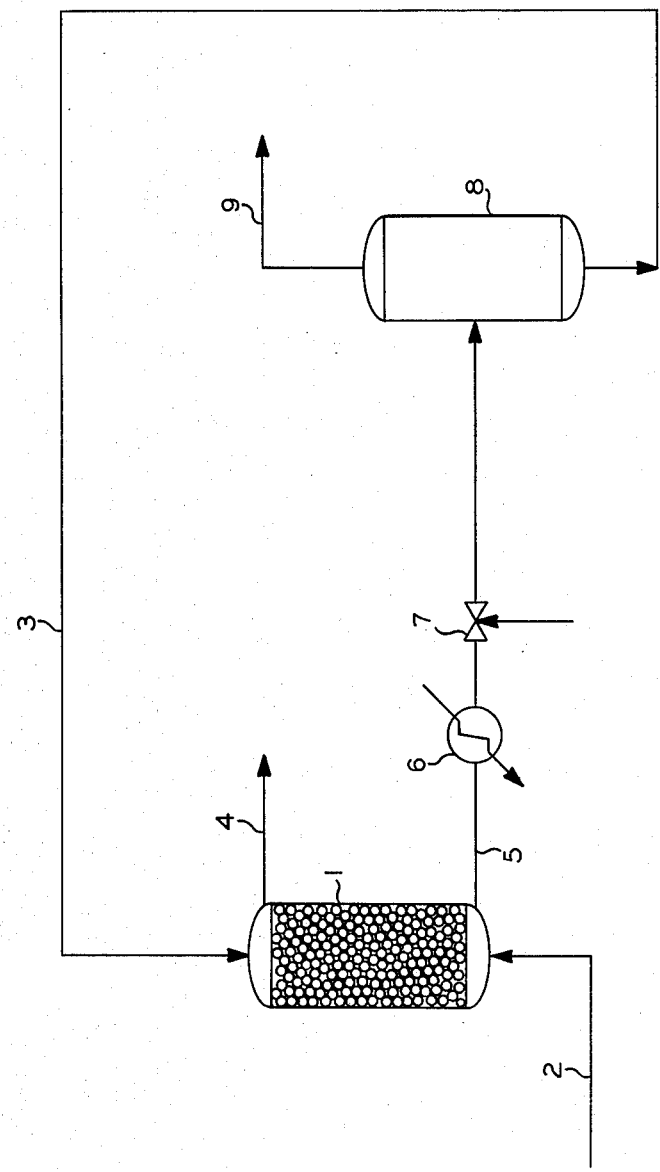

United States Patent [19]
Gordon et al.

[11] 4,348,214
[45] Sep. 7, 1982

[54] HYDROGEN SULFIDE REMOVAL WITH SULFUR-CONTAINING ESTERS

[75] Inventors: Bruce W. Gordon, Borger, Tex.; Edward E. Huxley, Fritch, Tex.

[73] Assignee: Phillips Petroleum Company, Bartlesville, Okla.

[21] Appl. No.: 249,547

[22] Filed: Mar. 31, 1981

[51] Int. Cl.³ ............................................. B01D 19/00
[52] U.S. Cl. .......................................... 55/48; 55/73; 141/1
[58] Field of Search .................. 55/73, 48; 423/243, 423/226; 560/147; 141/1

[56] References Cited

U.S. PATENT DOCUMENTS

| | | |
|---|---|---|
| 1,953,478 | 4/1934 | Hansen . |
| 2,268,185 | 12/1941 | Burke et al. ..................... 560/147 |
| 3,475,389 | 10/1969 | Jones . |
| 4,144,039 | 3/1979 | Blanc et al. ..................... 423/226 |
| 4,229,588 | 10/1980 | Louthan ........................... 560/147 |

FOREIGN PATENT DOCUMENTS 54-1288  1/1979  Japan ............................. 55/73

*Primary Examiner*—Bernard Nozick

[57] ABSTRACT

Sulfur-containing esters, such as dimethyldithiodipropionate, are excellent solvents for hydrogen sulfide and can be used for the purification of gas streams containing hydrogen sulfide. The obtained solution can be stored and used as H₂S source.

5 Claims, 1 Drawing Figure

HYDROGEN SULFIDE REMOVAL WITH SULFUR-CONTAINING ESTERS

BACKGROUND OF THE INVENTION

The removal of hydrogen sulfide from other fluids is a problem arising in a variety of industrial processes. Thus hydrogen sulfide is a byproduct in coal gasification. Hydrogen sulfide is also a common contaminant in natural gas streams. A variety of methods have been proposed to remove hydrogen sulfide from gas streams. There is a continued need for efficient ways to remove hydrogen sulfide from gas streams, particularly in view of environmental laws and the fact that hydrogen sulfide is a rather dangerous compound.

THE INVENTION

It is one object of this invention to provide a process for the removal of hydrogen sulfide from fluid streams, particularly from gas streams.

Another object of this invention is to provide a new group of selective solvents for hydrogen sulfide.

Still a further object of this invention is to provide a solution of hydrogen sulfide in a high concentration in a solvent.

Yet another object of this invention is to provide a process of low pressure $H_2S$ storage.

These and other objects, advantages, details, features and embodiments of this invention will become apparent to those skilled in the art from the following detailed description of the invention and the appended claims.

In accordance with this invention, it has been found that sulfur containing esters are good solvents for hydrogen sulfide.

Thus, in accordance with a first embodiment of this invention, a process for the removal of hydrogen sulfide from a gas stream is provided. In accordance with this process, the hydrogen sulfide-containing gas stream is contacted with a sulfur-containing ester such as to produce a hydrogen sulfide solution in this ester as well as a gas stream having reduced hydrogen sulfide content as compared to the starting material.

Broadly speaking, the solvent for hydrogen sulfide comprises one or more sulfur-containing esters such as esters of sulfur-containing acids. The esters useful in this invention can be defined as containing (a) 1 to 4, preferably 1 or 2 ester groups —COOR, wherein R is a hydrocarbyl radical, having 1 to 20 C atoms, preferably an alkyl radical, and (b) 1 to 6 sulfur groups selected from —SH and —(S)$_x$—, x being an integer of 1 to 6, preferably 1 to 4, most preferably 1 or 2. The sulfur groups and the ester groups are attached to one or more hydrocarbon structures each having 1 to 10 carbon atoms. The hydrocarbon structures are preferably alkyl structures. Generally, the ester group will be separated from the sulfur structure by one or more, preferably one or two carbon atoms.

Examples of the so-defined esters of sulfur-containing acids which are useful in accordance with this invention are alkyl esters of sulfur (—SH, —(S)$_x$—) containing aliphatic acids. Among the alkyl esters of sulfur-containing aliphatic acids are the presently preferred selective solvents for hydrogen sulfide, namely methyl 3-mercaptopropionate: $CH_3—O—CO—(CH_2)_2—SH$, dimethylthiodipropionate: $CH_3—O—CO—(CH_2)_2—S—(CH_2)_2—CO—O—CH_3$, and dimethyldithiodipropionate: $CH_3—O—CO(CH_2)_2—S—S—(CH_2)_2—CO—O—CH_3$. These preferred sulfur-containing esters have two carbon atoms or a 1,2-ethylene group between the sulfur group and the ester group.

The contacting of the hydrogen sulfide-containing fluid with the sulfur-containing ester or esters is carried out under standard conditions and in standard equipment. The specific process and equipment utilized depends to a significant degree upon the degree of hydrogen sulfide removal desired, the specific ester used as the selective solvent and the nature of the fluid from which the hydrogen sulfide is to be removed. Typically, the purification is carried out in a counter-current contacting column into which the ester of the mercapto acid is introduced at the top and the hydrogen sulfide-rich ester is withdrawn at the bottom. The gas stream containing hydrogen sulfide is introduced at the bottom of this column and the purified gas stream is withdrawn from the top. The contacting is usually carried out at a temperature above the melting point of the ester of the mercapto acid and normally under pressure conditions which correspond to the pressure of the gas stream to be purified. These conditions can be further characterized as follows:

Temperature Range: any temperature above freezing point and below the decomposition temperature of the specific ester or mixture of esters being used. Lower temperatures favor greater $H_2S$ solubility.

Pressure Range: anywhere from a vacuum to higher pressure can be used. Higher pressures increase $H_2S$ solubility. The pressure used is such as to keep the ester or ester mixture in the liquid phase at the operating temperature.

Since the sulfur-containing ester dissolves a very high quantity of hydrogen sulfide, the product obtained, namely the solution of the hydrogen sulfide in the sulfur-containing ester can be stored and used as a source for hydrogen sulfide in other chemical processes, e.g., by heating this solution to free dissolved hydrogen sulfide as a gas.

In accordance with a further embodiment there is thus provided an $H_2S$ solution which is usable as an $H_2S$ source. The $H_2S$ content of the solution lies in the range of 5 ppm to saturation. The $H_2S$ solution comprises the sulfur-containing ester (or a mixture of two or more of such esters) and $H_2S$. The quantity of hydrogen sulfide dissolved in the sulfur-containing ester solvent will preferably be between 1 vol. % (liquid volume) and saturation. Furthermore, an embodiment of this invention resides in a process to store $H_2S$. This process comprises contacting $H_2S$ gas or liquid with the sulfur-containing ester defined to obtain a solution as described above. This solution is then placed into a liquid storage vessel where it remains under a relatively low pressure and in equilibrium with an $H_2S$ containing atmosphere until it is used. The solution is readily usable as $H_2S$ source by simple heating it to release $H_2S$ gas.

In the gas purification process described above, it is preferred to pass the solution of sulfur-containing ester, which is rich in hydrogen sulfide, to a regeneration zone wherein hydrogen sulfide is removed from this rich solution by heating the solution and/or by subjecting the solution to reduced pressure. The so-regenerated mercapto acid ester is then recycled to the contacting step and reutilized.

In the drawing one such application of this invention is shown.

Into a packed column 1 a stream of natural gas containing H$_2$S is introduced at or near the bottom via conduit 2. A stream of liquid absorbent is introduced at or near the top of the column via line 3. A stream of natural gas being essentially free of H$_2$S removed via conduit 4 and passed to further use or storage. From the bottom of the column 1 H$_2$S containing absorbent is withdrawn via line 5. This rich absorbent stream is heated in heater 6, reduced in pressure at the pressure let-down valve 7 and passed to stripper 8. Lean adsorbent, i.e. essentially H$_2$S-free adsorbent, is withdrawn from the bottom of stripper 8 via line 3, H$_2$S gas is withdrawn from the top via line 9. The H$_2$S stream is passed to storage or further use whereas the lean adsorbent is recycled to extraction column 1.

Typical conditions in the extraction column 1 are:
Pressure: 100 to 500 psig
Temperature: 0° to 120° F., preferably ambient.

The following example is given to more fully illustrate the invention without undue limitation of its scope.

EXAMPLE

Crude dimethyldithiodipropionate (61.0 wt. % solution additionally containing 36.3 wt. % methyl 3-mercaptopropionate and 2.7 wt. % dimethylthiodipropionate) was saturated with H$_2$S at 80 F. and atmospheric pressure by dissolving liquid H$_2$S in the solvent under pressure and then reducing the pressure to atmospheric.

The saturated solution was vacuum distilled at 5 mm Hg to separate the H$_2$S. Based on the volume of recovered solvent it was determined that the saturated solution contained 13% (liquid volume) hydrogen sulfide.

Reasonable variations and modifications which will become apparent to those skilled in the art can be made from this invention without departing from the spirit and scope thereof.

We claim:

1. Process to remove hydrogen sulfide from a feed gas stream comprising contacting this feed gas stream with a solvent comprising at least one ester containing 1-4 ester groups COOR wherein R is a hydrocarbyl radical having 1-20 C atoms and containing one or more sulfur groups selected from the group consisting of —SH and —(S)$_x$—, x being an integer of 1 to 6, to produce a solution of hydrogen sulfide in said solvent and a gas stream having reduced hydrogen sulfide content as compared to the feed gas stream.

2. Process in accordance with claim 1 further comprising subjecting said solution of hydrogen sulfide in said solvent to a regeneration step to produce hydrogen sulfide and ester containing solvent essentially free of hydrogen sulfide and reintroducing said solvent essentially free of hydrogen sulfide into said contacting step.

3. Process in accordance with claim 2 wherein said ester contains 1 to 4 ester groups —COOR, wherein R is a hydrocarbyl radical having 1–20 carbon atoms, and 1 to 4 sulfur groups.

4. Process in accordance with claim 3 wherein said ester is an alkyl ester of a mercaptoaliphatic acid or of an acid-containing sulfide or polysulfide structures —(S)$_x$—.

5. Process to store hydrogen sulfide comprising
   (a) passing a hydrogen sulfide containing gas stream through an ester solvent comprising an ester containing 1-4 ester groups COOR wherein R is a hydrocarbyl radical having 1-20 C atoms and containing one or more sulfur groups selected from the group consisting of —SH and —(S)$_x$—x being an integer of 1 to 6, such as to dissolve hydrogen sulfide in said ester solvent and to form an H$_2$S solution,
   (b) passing the obtained H$_2$S solution to a storage vessel, and
   (c) maintaining the H$_2$S solution closed in this storage vessel and under an atmosphere in equilibrium with the H$_2$S solution.

* * * * *